United States Patent [19]

Gruber et al.

[11] Patent Number: 4,529,771

[45] Date of Patent: * Jul. 16, 1985

[54] COMPOSITION, METHOD FOR PREPARING AND USE THEREOF

[75] Inventors: Bruce A. Gruber, Worthington, Ohio; Diether Koch, Mettmann, Fed. Rep. of Germany; Heimo J. Langer; William R. Dunnavant, both of Columbus, Ohio

[73] Assignee: Ashland Oil, Inc., Ashland, Ky.

[ * ] Notice: The portion of the term of this patent subsequent to Nov. 20, 2001 has been disclaimed.

[21] Appl. No.: 575,254

[22] Filed: Jan. 30, 1984

Related U.S. Application Data

[63] Continuation-in-part of Ser. No. 524,050, Aug. 16, 1983, Pat. No. 4,483,961, which is a continuation-in-part of Ser. No. 300,786, Sep. 10, 1981, Pat. No. 4,412,088.

[51] Int. Cl.³ ...................... C08L 61/00; C08G 16/00
[52] U.S. Cl. ..................................... 524/542; 523/139; 523/144; 523/145; 524/593; 524/827; 528/220; 528/246
[58] Field of Search ................. 585/23, 357; 528/220, 528/246; 523/139, 144, 145; 524/542, 593, 877

[56] References Cited

U.S. PATENT DOCUMENTS

| | | | |
|---|---|---|---|
| 2,589,969 | 3/1952 | Schutze et al. | 585/357 |
| 3,051,765 | 8/1962 | McCain | 585/357 |
| 3,192,275 | 6/1965 | Freiesleben | 585/357 |
| 3,262,990 | 7/1966 | Hurwitz et al. | |
| 3,376,304 | 4/1968 | Mahrbacher et al. | 585/23 |
| 3,390,156 | 6/1968 | Hurwitz et al. | 585/23 |
| 4,246,167 | 1/1981 | Grimm et al. | 523/144 |
| 4,320,218 | 3/1982 | Gruber et al. | 260/998.18 |

OTHER PUBLICATIONS

McCain, J. Org. Chem., 23, 632, (1958).
Angus et al., J. Chem. Soc., 1409, (1960).
Neuenschwander et al, Helv. Chim. Acta, 46, 1760, (1963).
Meuche et al., Helv. Chim. Acta, 47, 1211, (1964).
Neuenschwander et al., Chimia, 35, 476, (1981).

*Primary Examiner*—Allan M. Lieberman
*Attorney, Agent, or Firm*—Pollock, Vande Sande & Priddy

[57] ABSTRACT

Thermosettable polymeric cyclopentadiene derivatives, method for preparing polymeric cyclopentadiene derivatives, and use of polymeric cyclopentadiene derivatives in curable binder compositions.

29 Claims, No Drawings

COMPOSITION, METHOD FOR PREPARING AND USE THEREOF

CROSS REFERENCE TO RELATED APPLICATION

This application is a continuation-in-part of our copending U.S. patent application Ser. No. 524,050, filed on Aug. 16, 1983, now U.S. Pat. No. 4,483,961 "Polymeric Cyclopentadiene Derivatives, Method for Preparing and Use Thereof" which in turn, is a continuation-in-part of U.S. patent application Ser. No. 300,786, filed on Sept. 10, 1981 and entitled "Cyclopentadiene Derivatives, Method for Preparing and Use Thereof", now U.S. Pat. No. 4,412,088.

DESCRIPTION

1. Technical Field

The present invention is directed to new thermosetting polymeric cyclopentadiene derivatives which are particularly useful in binder compositions. Such compositions are curable to a thermoset state at normal room temperatures. The compositions are capable of being cured at normal room temperatures by a gaseous curing agent or an acidic catalyst incorporated into the binder. The compositions of the present invention are especially useful as foundry binders. The present invention is also directed to a method for preparing the thermosettable polymeric derivatives of cyclopentadiene.

2. Background Art

In the foundry art, cores and molds used in making metal castings are generally prepared from shaped, cured mixtures of aggregate material (e.g. sand) and a binder. One of the preferred techniques of making these sand cores includes the basic steps of mixing the sand with a resin binder and a curing catalyst, molding the mixture to the desired shape and allowing it to cure and solidify at room temperature without the application of heat. Resins useful in this technique include furfuryl alcohol-formaldehyde polymers, furfuryl alcohol-urea-formaldehyde polymers, alkyd isocyanate resins, and sodium silicate binders. Such technique is commonly referred to as a "no bake" process.

Another technique employed includes the basic steps of mixing the aggregate with a resin binder, molding the mixture to the desired shape, and curing the shape by passing a gaseous catalyst through it. This technique is often referred to as the "cold box" method. Binders which are suitable for use in such processes must possess a number of important characteristics. For instance, the binders must be capable of providing relatively high strength characteristics to the molded article and must be capable of curing to a considerable degree at normal room temperatures. Also, since curing of the binders occurs while as a thin layer of film on the aggregate and the aggregate can act as a heat sink, the curing does not necessarily proceed in the same manner as when the binder is cured in bulk. In addition, foundry cores and molds must retain the strength properties until the metal solidifies in the mold, but must lose such properties due to their exposure at higher temperatures so that after solidification of the metal the cores or molds can readily be broken down for shake-out or removal from the casting. Accordingly, providing new binders for foundry applications which contain the necessary properties is quite difficult. This problem is made more acute when the object is a relatively inexpensive binder.

It has also been discovered that fulvenes and/or fulvene prepolymers could be employed as binders for foundry applications as described in U.S. Pat. No. 4,246,167 entitled "Foundry Binder Composition" to Grimm, et al. and assigned to Ashland Oil, Inc., the assignee of the present application. However, the use of such fulvenes has not been entirely satisfactory since such are somewhat susceptible to degradation from atmospheric oxygen and have an unpleasant odor.

In addition, applicants in U.S. Pat. No. 4,412,088 disclose certain derivatives of cyclopentadiene and/or of methyl cyclopentadiene which have improved resistance to atmospheric oxygen and reduced odor as compared to the fulvenes discussed hereinabove.

In copending application Ser. No. 524,050, applicants disclose polymeric cyclopentadiene derivatives which have greater erosion resistance when compared to the use of the fulvenes and cyclopentadiene derivatives mentioned above.

DISCLOSURE OF INVENTION

The present invention provides a process for preparing certain thermosettable polymeric derivatives of cyclopentadiene and/or of methyl substituted cyclopentadiene. The present invention is also concerned with novel thermosettable polymeric derivatives of cyclopentadiene and/or of methyl substituted cyclopentadiene which can be produced by the process of the present invention. The present invention is also concerned with the use of certain thermosettable polymeric derivatives of cyclopentadiene and/or of methyl substituted cyclopentadiene in binder compositions and especially foundry binder compositions.

The polymers of the present invention have reduced odor as compared to the fulvenes and the cyclopentadiene derivatives discussed hereinabove. Moreover, the polymers of the present invention, when used in a binder composition for molded articles, demonstrate substantially no erosion tendency.

Moreover, the thermosettable polymers of the present invention, when used in a binder composition for foundry shapes, provide for good surface finishing of the metal cast in the foundry shape. Furthermore, reduced smoke has been observed in iron castings employing foundry shapes with the polymers of the present invention.

The present invention is concerned with polymeric cyclopentadiene derivatives having recurring units of the Formula I, or isomers thereof, or mixtures thereof:

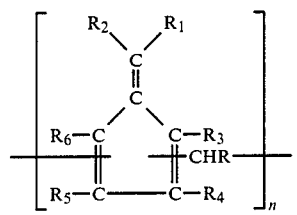

R is hydrogen or an alkyl group having 1-4 carbon atoms. Each $R_1$ and $R_2$, individually, is methyl or ethyl, or both $R_1$ and $R_2$ are hydrogen atoms. Each $R_3$, $R_4$, $R_5$, and $R_6$, individually, is hydrogen, or methyl, or —CH$_2$—, or

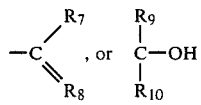

provided that at least one of $R_3$, $R_4$, $R_5$, and $R_6$ is hydrogen. It is further provided that at least two of said $R_3$, $R_4$, $R_5$, and $R_6$ are —CHR—. $R_7$ is hydrogen, or methyl, or ethyl. $R_8$ is methylene or ethylidene. Each $R_9$ and $R_{10}$, individually, is hydrogen, or methyl, or ethyl. In addition, n is an integer of at least 2.

The present invention is also concerned with a curable composition which includes at least one thermosettable polymeric cyclopentadiene derivative of the type discussed hereinabove and an acidic catalyst. The acidic catalyst has a pKa of about 4 or less and is considered a proton donor. The acidic catalyst is incorporated into the composition prior to molding or is provided by passing a gas through the molded composition.

The present invention is also concerned with molding compositions which include a major amount of aggregate and an effective bonding amount up to about 40% by weight of the aggregate of the above-defined curable composition.

The present invention is also directed to a process for the fabrication of molded articles which includes the following steps:
(a) mixing aggregate with a bonding amount up to about 40% by weight based upon the weight of the aggregate of a binder composition of the type described hereinabove which contains the acidic catalyst;
(b) introducing the composition obtained from step (a) into a pattern;
(c) hardening the composition in the pattern to become self-supporting; and
(d) thereafter removing the shaped article of step (c) from the pattern and allowing it to further cure, thereby obtaining a hardened, solid, cured, molded article.

The present invention is also concerned with a process for the fabrication of molded articles which comprises:
(a) mixing the aggregate with a bonding amount up to about 40% by weight based upon the weight of the aggregate of a polymeric cyclopentadiene derivative of the type discussed hereinabove;
(b) introducing the composition obtained from step (a) into a pattern;
(c) hardening the composition in the pattern to become self-supporting by passing an acidic gas through the composition; and
(d) thereafter removing the shaped article of step (c) from the pattern and allowing it to further cure, thereby obtaining a hardened, solid, cured, molded article.

The present invention is also concerned with a process for casting a metal which includes fabricating a shape as described hereinabove, pouring metal while in the liquid state into or around the shape, allowing the metal to cool and solidify, and then separating the molded metal article.

The present invention is also concerned with a process for preparing thermosettable polymeric cyclopentadiene derivative which comprises reacting a cyclopentadiene derivative having the formula:

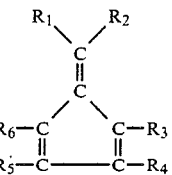

isomers, or mixtures thereof; wherein each $R_1$ and $R_2$, individually, is methyl, or ethyl, or both $R_1$ and $R_2$ are hydrogen. Each $R_3$, $R_4$, $R_5$, and $R_6$, individually, is hydrogen, methyl, or

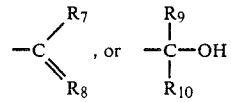

wherein each $R_7$ is hydrogen, methyl, or ethyl; and $R_8$ is methylene or ethylidene. Each $R_9$ and $R_{10}$, individually, is hydrogen, or methyl, or ethyl; with an aldehyde having 1-5 carbon atoms in the presence of a basic catalyst to provide a polymeric cyclopentadiene derivative.

The reaction is carried out at a temperature of about 60° C. or less. The reaction is usually completed in about 4 hours or less.

Moreover, the present invention is directed to thermosettable polymeric cyclopentadiene derivatives obtained by the process described hereinabove.

BEST AND VARIOUS MODES FOR CARRYING OUT INVENTION

The polymeric cyclopentadiene derivatives of the present invention are represented by the recurring Formula I below, or isomers or mixtures thereof:

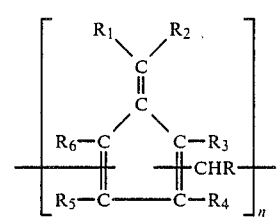

R is hydrogen or an alkyl containing 1–4 carbon atoms. R is preferably hydrogen or methyl and most preferably is hydrogen. Each $R_1$ and $R_2$, individually, is methyl, or ethyl, or both $R_1$ and $R_2$ are hydrogen. Preferably at least one of $R_1$ and $R_2$ is methyl. Each $R_3$, $R_4$, $R_5$, and $R_6$, individually, is hydrogen, or methyl, or $R_7$—C=$R_8$, or

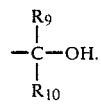

At least one of $R_3$, $R_4$, $R_5$, and $R_6$ is hydrogen. At least two of said $R_3$, $R_4$, $R_5$, and $R_6$ are —CHR—. $R_7$ is hydrogen, or methyl, or ethyl. $R_8$ is methylene or ethylidene. Each $R_9$ and $R_{10}$, individually, is hydrogen, or methyl, or ethyl. Preferably, at least one of $R_7$ and $R_8$ differs from $R_1$ and $R_2$. Preferably at least one $R_7$ and $R_8$ is methyl. When a $R_7$—C=$R_8$ group is present, such is preferably at the $R_4$ or $R_5$ position.

In addition, if excess aldehyde or ketone is employed in the preparation of the monomeric cyclopentadiene derivatives, such could contain compounds wherein $R_3$, $R_4$, $R_5$, or $R_6$ can have the structure:

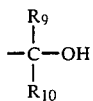

n is at least 2 and preferably at least 15. The average n is usually about 2 to about 25.

An example of an isomer of Formula I above can be represented by the structure:

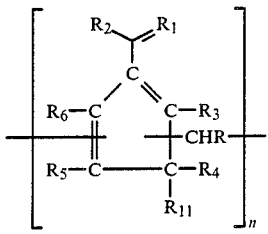

wherein R is hydrogen or alkyl of 1–4 carbon atoms; $R_1$ is methylene or ethylidene; $R_2$ is methyl or ethyl; each $R_3$, $R_4$, $R_5$, $R_6$, and $R_{11}$, individually, is hydrogen, methyl, or

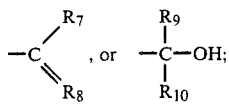

wherein $R_7$ is hydrogen, or methyl, or ethyl; $R_8$ is methylene or ethylidene; each $R_9$ and $R_{10}$, individually, is hydrogen, or methyl, or ethyl; and provided that at least 2 of $R_3$, $R_4$, $R_5$, $R_6$, and $R_{11}$ are hydrogen.

Examples of some cyclopentadiene derivatives from which ther thermosettable polymeric cyclopentadiene derivatives of the present invention can be obtained include fulvenes such as methylethylfulvene ($R_1$ is methyl; $R_2$ is ethyl; $R_3$, $R_4$, $R_5$, and $R_6$ are H); and dimethyl fulvene ($R_1$ and $R_2$ each are methyl; $R_3$, $R_4$, $R_5$, and $R_6$ are H).

In addition, fulvenes can be purified by distillation according to a method by Kice, J.A.C.S. 80, 3792 (1958), and the method of McCaine, J. Organic Chemistry 23, 632 (1958).

The thermosettable polymeric cyclopentadiene derivatives of the present invention can be prepared by reacting a fulvene of the formula:

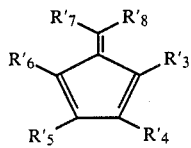

wherein each $R'_7$ and $R'_8$, individually, is methyl, or ethyl, or both $R'_7$ and $R'_8$ are hydrogen. Each $R'_3$, $R'_4$, $R'_5$, and $R'_6$, individually, is hydrogen or methyl, or

provided that a maximum of only one such $R'_3$, $R'_4$, $R'_5$, and $R'_6$ is methyl, and at least two of $R'_3$, $R'_4$, $R'_5$, and $R'_6$ are hydrogen, and in addition, if excess aldehyde or ketone is employed in the preparation of the fulvene, $R'_3$, $R'_4$, $R'_5$, or $R'_6$ can have the structure

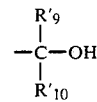

wherein each $R'_9$ and $R'_{10}$, individually, is hydrogen, or methyl, or ethyl and wherein $R'_1$ is hydrogen or methyl or ethyl and $R'_2$ is methylene or ethylidene.

The fulvene can be prepared by reacting cyclopentadiene and/or methylcyclopentadiene with a carbonyl compound from the group of aldehyde or ketone in the presence of a basic catalyst. The carbonyl compounds have 2 to 5 carbon atoms and more preferably, are ketones having a hydrogen on the alpha carbon atom, and most preferably are ketones with at least one methyl group. The reaction is generally carried out at temperatures of about 25°–90° C. and preferably at about 25°–80° C. Examples of some basic catalysts include: strong bases (e.g. KOH), amines, and basic ion exchange resins. Suggestions of methods for preparing fulvenes can be found in U.S. Pat. Nos. 2,589,969; 3,051,765; and 3,192,276. It is also known that fulvenes polymerize in the presence of acids. Suggestions of preparing fulvene polymers can be found in U.S. Pat. Nos. 2,512,698; 2,587,791; 2,898,325; and 3,390,156. The amount of catalyst employed is usually about 20 to about 50 mole percent based on the moles of cyclopentadiene or methylcyclopentadiene used.

About stoichiometric amounts (e.g. a maximum of about a 10% excess of either reactants) are usually employed. The reaction is preferably carried out in an alcoholic solution. The reaction usually takes about 0.5 to about 3 hours. The amount of diluent (e.g. alcohols such as methanol, ethanol, isopropanol, n-propanol, butanols, and amyl alcohol) is usually about 50 to about 150 ml/mole of cyclopentadiene or methylcyclopentadiene. Preferably, a mixture of methanol with higher alcohols having 3 or more carbon atoms is employed.

Thermosettable polymeric derivatives within the scope of the present invention can be prepared by either of the following two procedures:

1. The reaction product from the above-discussed type of reaction (i.e. the fulvene) is reacted with an aldehyde having 1–5 carbon atoms, as will be discussed hereinbelow to provide the polymers of the present invention.

2. The reaction product from the above-discussed type of reaction (i.e. the fulvene) is reacted with a carbonyl compound in general (e.g. acetone and methylethyl ketone) to provide a disubstituted cyclopentadiene of the type disclosed in U.S. Pat. No. 4,412,088, disclosure of which is incorporated herein by reference. This reaction is also carried out in the presence of a basic catalyst of the type and amounts discussed hereinabove, employed to prepare the fulvenes.

The carbonyl compounds contain 2 to 5 carbon atoms and preferably are ketones containing at least one methyl group. The most preferred ketone is acetone.

This reaction is generally carried out at temperatures of about 25°–90° C. and preferably at about 25°–80° C. Generally, about 0.25 to about 1.5 times the stoichiometric amount of the carbonyl compound is used and preferably about stoichiometric amounts (e.g. about a maximum of a 10% excess of either reactant) of the reactants employed. However, when acetone is used as the only carbonyl compound in both stages of the process, up to a two-fold amount of acetone is preferably employed. This reaction is preferably carried out in an alcoholic solution. The reaction usually takes about 1 to about 24 hours. The amounts of catalyst and diluent are usually within the same range as those amounts employed in preparing the fulvene.

By following the above process, a mixture containing about 30–60% of disubstituted cyclopentadiene derivatives of the type disclosed in U.S. Pat. No. 4,412,088 can be obtained.

The reaction products containing the disubstituted cyclopentadiene derivatives is reacted with an aldehyde having 1–5 carbon atoms, as will be discussed hereinbelow to provide the thermosettable polymers of the present invention.

Mixtures of any of the above fulvenes and/or disubstituted cyclopentadiene derivatives can be employed, if desired.

The fulvene and/or disubstituted cyclopentadiene derivative is then reacted with an aldehyde having 1–5 carbon atoms to provide the polymeric derivatives of the present invention. The preferred aldehydes are formaldehyde and acetaldehyde. The most preferred aldehyde is formaldehyde. Generally, about 0.1 to about 2 moles of aldehyde and preferably, about 0.5 to about 1.25 moles of aldehyde are employed for each mole of cyclopentadiene type reactant. In the reaction with the aldehyde, substituted cyclopentadiene derivatives may form disubstituted derivatives wherein one of the substitutions is due to the aldehyde. Also, in cases when no excess acetone is used to prepare the fulvene, some unreacted cyclopentadiene will remain and react with the aldehyde to form monosubstituted cyclopentadiene. For instance, in the case of formaldehyde and when no excess acetone is used to prepare the fulvene, some unreacted cyclopentadiene will remain and react with the formaldehyde to form monosubstituted cyclopentadiene wherein $R_1$ and $R_2$ are hydrogen. These materials also provide polymeric derivatives in accordance with the present invention.

The formaldehyde, when employed, is preferably in the form of a methanol solution. However, other forms capable of supplying formaldehyde to the reaction mass such as paraformaldehyde and trioxane can be employed.

Paraformaldehyde is a substantially water-free source of formaldehyde and is a mixture of polyoxymethylene glycol which usually contains from about 90 to about 99% by weight of formaldehyde with the balance consisting principally of free and combined water, as long as the mixture is still a solid material. Usually, commercial grades of paraformaldehyde contain from about 91 to about 98% formaldehyde. The chemical composition of paraformaldehyde can be expressed by the following formula:

$$HO(CH_2O)_nH$$

wherein n is equal to 8 to 100. Normally, the majority of the polyoxymethylene glycols in paraformaldehyde contain over about 12 formaldehyde units per molecule. Paraformaldehyde has a melting point of from about 120° to about 170° C.

This reaction is also carried out in the presence of a basic catalyst of the type and amounts discussed hereinabove employed to prepare the fulvenes.

This reaction must be carried out at temperatures of about 60° C. or less and preferably at about 45°–60° C.

Temperatures of about 60° C. or less are employed to insure against gellation during the reaction. When the solvent employed is a mixture of methanol and a higher alcohol such as isopropanol, it is preferred that the maximum temperature be about 50° C. When the solvent is methanol, the preferred maximum temperature is about 60° C. This reaction is preferably carried out in an alcoholic solution. The reaction usually takes about one-fourth to about 4 hours and preferably about one-half to about 3 hours. It is important to employ reaction times of about 4 hours or less in order to insure against gellation occurring.

The amounts of catalyst and diluent are usually within the same range as those amounts employed in preparing the fulvene.

By following the above procedures, the polymeric derivatives of the present invention are obtained. The polymeric derivatives have molecular weights up to about 250,000 and n in FIG. I is an integer up to about 1800. The polymeric derivatives preferably have average molecular weights of about 200 to about 4000 and preferably the average n in Formula I is an integer of about 2 to about 25.

Furthermore, the polymers can be reacted with ketones and preferably acetone in the presence of a basic catalyst under the same conditions as described hereinabove for the reaction of the fulvenes with the carbonyl compound to provide the disubstituted cyclopentadiene derivatives.

The polymers preferably are fluid enough so that such, when applied either per se, or in admixture with the diluents, flow to coat the aggregate used.

The thermosettable polymeric cyclopentadiene derivatives of the present invention are especially useful in binder compositions and particularly foundry binder composition. Mixtures of the polymeric cyclopentadiene derivatives can be used.

The thermosettable polymers of the present invention demonstrate considerable resistance to elevated temperatures and to erosion during casting when employed in a foundry shape. Furthermore, reduced smoke formulation in iron castings has been observed during the casting of iron. The thermosettable polymers of the present invention also exhibit reduced odor.

In addition, the binder composition of the present invention contains an acidic catalyst. The acidic catalysts employed have a pKa value of about 4 or less and are proton donors and include organic acids such as formic acid, oxalic acid, and the organic substituted sulfonic acids such as benzenesulfonic acid and toluenesulfonic acid, and Lewis acids such as $BF_3$. The preferred catalysts are the organic substituted sulfonic acids. The acidic catalyst can be provided in the foundry mix before molding (e.g. "no bake" and "warm box" processes) and/or by passing a gas through the molded composition such as an acid per se or a gas such as $SO_2$ which, in conjunction with a component of the molded composition (e.g. a peroxide), forms an acid in situ.

The acidic catalyst, when already in the mix, prior to molding, is generally present in amounts up to a maximum of about 15% by weight based upon the amount of binder employed. The minimum amount of acidic catalyst is usually about 4% based upon the amount of binder employed. When employing a "cold box" process, usually up to about 5 seconds of gassing time is sufficient.

Furthermore, binder compositions of the present invention can be used in a "warm box" process at temperatures of about 300° F. to about 400° F.

The thermosettable polymeric cyclopentadiene derivatives can be employed in combination with fulvenes of the type discussed hereinabove, and/or with disubstituted cyclopentadiene derivatives, and/or prepolymers thereof, as discussed in U.S. Pat. No. 4,412,088, and/or with furfuryl alcohol, and/or furan prepolymer foundry binder systems, and/or phenolic materials such as phenol, substituted phenols, or phenolformaldehyde condensates.

The furan prepolymers include reaction products of furfuryl alcohol and of aldehydes such as formaldehyde. In addition, the aldehyde-furfuryl alcohol reaction product can be modified with varying amounts of reactants such as urea. The mole ratios of formaldehyde to furfuryl alcohol which can be employed can vary widely. For instance, the furan polymer can be prepared from about 0.4 to about 4 moles of furfuryl alcohol per mole of formaldehyde, and preferably from about 0.5 to about 2 moles of furfuryl alcohol per mole of formaldehyde.

The furan polymer which can be employed in the present invention can be any of the various furan polymers which are known to be suitable for molding and especially foundry purposes. Examples of such furan polymers include those obtained from about 1 mole of urea, about .0.2 to 2 moles of furfuryl alcohol, and about 1 to 3 moles of formaldehyde such as described in U.S. Pat. Nos. 3,222,315 and 3,247,556. Other suitable furan polymers are disclosed in U.S. Pat. No. 3,346,534. The furan polymers are usually prepared by polymerization in the presence of an acid catalyst. Usually when a furan polymer is employed, it is added together with furfuryl alcohol.

When the polymeric cyclopentadiene derivatives are employed in admixture with other materials of the type discussed above, as auxiliary binders, such as furfuryl alcohol, and/or disubstituted cyclopentadiene derivatives, and/or fulvenes, and/or furan polymers, and/or phenolics, such polymeric cyclopentadiene derivatives are generally employed in amounts of about 90% to about 10% by weight based upon the total amount of polymeric cyclopentadiene derivative and other materials defined above.

When preparing an ordinary sand-type foundry shape the aggregate employed has a particle size large enough to permit sufficient porosity in the foundry shape to permit escape of volatiles from the shape during the casting operation. The term "ordinary sand-type foundry shapes" as used herein, refers to foundry shapes which have sufficient porosity to permit escape of volatiles from it during the casting operation. Generally, at least about 80% and preferably about 90% by weight of aggregate employed for foundry shapes has an average particle size no smaller than about 150 mesh (Tyler screen mesh). The aggregate for foundry shapes preferably has an average particle size between about 50 and about 150 mesh (Tyler screen mesh). The preferred aggregate employed for ordinary foundry shapes is silica sand wherein at least about 70 weight percent and preferably at least about 85 weight percent of the sand is silica. Other suitable aggregate materials include zircon, olivine, aluminosilicate sand, chromite sand, and the like.

When preparing a shape for precision casting, the predominant portion and generally, at least about 80% of the aggregate, has an average particle size no larger than about 150 mesh (Tyler screen mesh). Preferably, at least about 90% by weight of the aggregate for precision casting applications has a particle size no larger than 150 mesh and preferably between 325 mesh and 200 mesh. The preferred aggregates employed for precision casting applications are fused quartz, zircon sands, magnesium silicate sands, such as olivine and aluminosilicate sands.

Shapes for precision casting differ from ordinary sand-type foundry shapes in that the aggregate in shapes for precision casting can be more densely packed than the aggregate in shapes for ordinary sand-type foundry shapes. Therefore, shapes for precision casting must be heated before being utilized to drive off volatizable material present in the molding composition. If the volatiles are not removed from a precision casting shape before use, vapor created during casting will diffuse into the molten melt, since the shape has a relatively low porosity. The vapor diffusion would decrease the smoothness of the surface of the precision cast article.

When preparing a refractory such as ceramic, the predominant portion and at least about 80% by weight of the aggregate employed has an average particle size under 200 mesh and preferably no larger than 325 mesh. Preferably at least about 90% by weight of the aggregate for a refractory has an average particle size under 200 mesh and preferably no larger than 325 mesh. The aggregate employed in the preparation of refractories must be capable of withstanding the curing temperatures such as above about 1500° F. which are needed to cause sintering for utilization.

Examples of some suitable aggregate employed for preparing refractories include the ceramics such as refractory oxides, carbides, nitrides; and silicides such as aluminum oxide, lead oxide, chromic oxide, zirconium oxide, silica, silicon carbide, titanium nitride, boron nitride, molybdenum disilicide; and carbonaceous material such as graphite. Mixtures of the aggregates can also be used, when desired, including mixtures of metals and the ceramics.

Examples of some abrasive grains for preparing abrasive articles include aluminium oxide, silicon carbide, boron carbide, corundum, garnet, emery, and mixtures thereof. The grit size is of the usual grades as graded by the United States Bureau of Standards. These abrasive materials and their uses for particular jobs are understood by persons skilled in the art and are not altered in the abrasive articles contemplated by the present invention. In addition, inorganic filler can be employed along with the abrasive grit in preparing abrasive articles. It is preferred that at least about 85% of the inorganic fillers has an average particle size no greater than 200 mesh. It is most preferred that at least about 95% of the inorganic filler has an average particle size no greater than 200 mesh. Some inorganic fillers include cryolite, fluorospar, silica, and the like. When an organic filler is employed along with the abrasive grit, it is generally present in amounts from about 1 to about 30% by weight based upon the combined weight of the abrasive grit and inorganic filler.

In molding compositions, the aggregate constitutes the major constituent and the binder constitutes a relatively minor amount. In ordinary sand type foundry applications, the amount of binder is generally no greater than about 10% by weight and frequently within the range of about 0.5 to about 7% by weight based upon the weight of the aggregate. Most often, the binder content ranges from about 0.6 to about 5% by weight based upon the weight of the aggregate in ordinary sand type foundry shapes.

In molds and cores for precision casting application, the amount of binder is generally no greater than about 40% by weight and frequently within the range of about 5 to about 20% by weight, based upon the weight of the aggregate.

In refractories, the amount of binder is generally no greater than about 40% by weight and frequently within the range of about 5% to about 20% by weight based upon the weight of the aggregate.

In abrasive articles, the amount of binder is generally no greater than about 25% by weight and frequently within the range of about 5% to about 15% by weight based upon the weight of the abrasive material or grit.

A valuable additive to the binder compositions of the present invention in certain types of sand is a silane having the general formula:

wherein R' is a hydrocarbon radical and preferably an alkyl radical of 1 to 6 carbon atoms and R is a hydrocarbon group such as a vinyl group or an alkyl radical; an alkoxy-substituted alkyl radical; or an alkyl-amine-substituted alkyl radical in which the alkyl groups have from 1 to 6 carbon atoms. The aforesaid silane when employed in concentrations of about 0.05 to 2% based on the binder component of the composition improves the humidity resistance of the system.

Examples of some commercially available silanes are Dow Corning Z67040; Union Carbide A187 (gamma glycidoxy propyltrimethoxy silane); Union Carbide A1100 (gamma amino-propyltriethoxy silane); Union Carbide A1120 [N-beta(amino-ethyl)-gamma amino-propyltrimethoxy silane]; and vinyltriethoxysilane.

When the compositions of the present invention are used to prepare ordinary sand type foundry shapes, the following steps are employed:

1. Forming a foundry mix containing an aggregate (e.g. sand) and the bonding agent;
2. Introducing the foundry mix into a mold or pattern to thereby form the desired shape.
3. Allowing the shape to obtain a minimum strength in the mold; and
4. Thereafter removing the shape from the mold or pattern allowing it to further cure, thereby obtaining a hard, solid, cured foundry shape.

The foundry mix can optionally contain other ingredients such as iron oxide, ground flax fibers, wood cereals, pitch, refractory flours, and the like.

The systems of the present invention can be used for the casting of the relatively high melting point ferrous-type metals such as iron and steel which are poured at about 2500° F., as well as for the casting of the relatively low melting point nonferrous type metals such as aluminum, copper, and copper alloys including brass.

In order to further understand the present invention, the following non-limiting examples concerned with foundry are provided. All parts are by weight unless the contrary is stated. The foundry samples are cured by the so-called "no bake" process unless the contrary is stated.

Examples 1-4 represent preparations of thermosettable polymeric cyclopentadiene derivatives of the present invention.

EXAMPLE 1

Into a 1 liter, 3-neck flask equipped with a stirrer, condenser, thermometer, and $N_2$-inlet are added about 33.6 grams of KOH dissolved in about 45 ml of methanol and about 75 ml of isopropyl alcohol. At room temperature, about 104 grams (about 1.57 moles) of freshly distilled cyclopentadiene, which is kept at the temperature of dry ice/acetone, are added and the mixture is allowed to warm up to about 21° C. Next, about 87 grams (about 1.5 moles) of acetone are added over a period of 13 minutes.

The reaction mass is stirred for about 55 minutes at about 21° C. Next, about 81.9 grams of 55% methylformcel is added in about 8 minutes. The temperature rises to 47° C. for 30 minutes.

The solution is neutralized with dilute HCl and the water layer discarded. The residual solvent is stripped off employing pressure of about 20 inch Hg (23 mmHg) and 50° C. reactor temperature.

The polymeric material obtained is diluted to about 79% solids with HiSol 10. The diluted composition has a viscosity at 25° C. of 48 cps. No free formaldehyde is detected. The residual monomer concentration is about 28%. The average molecular weights are: $\overline{M}_w$ 3044; $\overline{M}_n$ 162 (by GPC analysis).

EXAMPLE 2

Into a 1 liter, 3-neck flask equipped with a stirrer, condenser, thermometer, and $N_2$-inlet, are added about 45 ml of methanol, about 75 ml of isopropyl alcohol, and about 33.6 grams of KOH. At room temperature are added about 159 grams of distilled methylethylidene cyclopentadiene. Next, about 62.25 grams of acetone are added in about 5 minutes. The reactor is heated to 50° C. for 50 minutes. The reactor is then cooled to 40° C. and about 81.9 grams of 55% methylformcel is added in 30 minutes while maintaining the temperature below 50° C. The reaction is continued for about 30 minutes.

The solution is neutralized with dilute HCl and the water layer discarded. The residual solvent is stripped off, employing pressure of about 29 inch Hg (23 mmHg) and 50° C. reactor temperature.

The polymeric material obtained is diluted to about 70% solids with HiSol 10. The diluted polymer has a viscosity at 25° C. of 77 cps. No free formaldehyde is detected. The residual monomer concentration is 9.2%. The average molecular weights are: $\overline{M}_w$ 3840; $\overline{M}_n$ 193 (by GPC analysis).

EXAMPLE 3

Into a 1 liter, 3-neck flask equipped with a stirrer, condenser, thermometer, and $N_2$-inlet are added about 45 ml of methanol, about 75 ml of isopropyl alcohol, and about 33.6 grams of KOH. At room temperature are added about 104 grams of freshly distilled cyclopentadiene. Next, about 43.5 grams of acetone and about 54 grams of methyl ethyl ketone are added in about 12 minutes while maintaining the temperature below 40° C. The reaction mass is stirred at 25°–30° C. for 2 hours and 20 minutes. Next, about 81.8 grams of methylformcel are added in 15 minutes. The reaction mass is maintained at 50° C. for another 30 minutes and then cooled to 25° C.

The solution is neutralized with dilute HCl and the water layer discarded. The residual solvent is stripped off, employing pressure of about 29 inch Hg (23 mmHg) and 50° C. reactor temperature.

The polymeric material obtained is diluted to about 70% solids with HiSol 10. The diluted polymer has a viscosity at 25° C. of 77 cps. No free formaldehyde is detected. The residual monomer concentration is 36%. The average molecular weights are: $\overline{M}_w$ 3856 and $\overline{M}_n$ 162 (by GPC analysis).

EXAMPLE 4

Into a 1 liter, 3-neck flask equipped with a stirrer, condenser, thermometer, and $N_2$-inlet are added about 33.6 grams of KOH dissolved in about 45 ml of methanol and about 75 ml of isopropyl alcohol. At room temperature, about 100 grams (about 1.51 moles) of freshly distilled cyclopentadiene, which is kept at the temperature of dry ice/acetone, are added. Next, about 87 grams (about 1.51 moles) of acetone are added over a period of 11 minutes.

The reaction mass is stirred for about 59 minutes at 22° C. Next, about 120 grams of 55% acetaldehyde in methanol is added in about 10 minutes. The temperature rises to 40° C. for 30 minutes. The solution is neutralized with dilute HCl and the water layer is discarded. The residual solvent is stripped off employing pressure of about 29 inch Hg (19 mmHg) and 45° C. reactor temperature.

The polymeric material obtained is diluted to about 60% solids with HiSol 10. The diluted composition has a viscosity at 25° C. of 5.3 cps. The residual monomer concentration is about 44%. The average molecular weights are: $\overline{M}_w$ 591 and $\overline{M}_n$ 215.

EXAMPLES 5–8

Foundry sand mixes are prepared by admixing sand with the binder compositions shown in Table 1 below. The resulting foundry sand mixes are then formed into standard AFS tensile test samples using the standard procedures. The cured samples are tested for tensile strength and hardness.

The binder compositions are employed in an amount of about 1.5% by weight, based upon the weight of the sand. The catalyst employed is a mixture of about 91% of a 62% aqueous solution of p-toluene sulphonic acid and 9% water, and is employed in amounts of about 22% by weight, based upon the binder composition. The amounts are in weight percent.

TABLE 1

EXAMPLES 5–8
COMPOSITION AND TENSILE STRENGTH

| | | | | |
|---|---|---|---|---|
| (A) Substituted Thermosettable Cyclopentadiene Polymers | | | | |
| Polymer prepared according to Example 1 | 54.1 | | | |
| Polymer prepared according to Example 2 | | 48.7 | | |
| Polymer prepared according to Example 3 | | | 56 | |
| Polymer prepared according to Example 4 | | | | |
| (B) Furfuryl Alcohol | 29 | 29.9 | 29.9 | 30 |
| (C) HiSol 10 | 16.3 | 20.9 | 20.9 | 14 |
| (D) Silane 1506 (Kayfries) | 0.5 | | | 0.25 |
| (E) Silane A-1102 | | 0.5 | 0.5 | |
| Work Time/Strip Time | 5"/26"–12'/50'–11'/29'–5'/41' | | | |
| Tensiles (PSI) | | | | |
| 1 Hour | 130 | 240 | 132 | 62 |
| 3 Hours | 208 | 347 | 197 | 108 |
| 24 Hours | 328 | 420 | 273 | 125 |
| 24 Hours + 24 Hours at 100% R.H. | 67 | 135 | 120 | 65 |

EXAMPLE 9

A foundry sand mixture is prepared by admixing sand with a binder composition containing about 48.6% by weight of the polymeric composition from Example 2, about 29.7% furfuryl alcohol, about 20.8% HiSol 10, and 0.9% silane. The amount of binder employed is about one and one-half weight % based upon the amount of sand. About 12.5% based upon the weight of binder of a catalyst are added. The resulting foundry sand mix is then formed into a standard AFS tensile test sample using the standard procedure. The mix is subjected to a "warm box" cure at a box temperature of 325° F. The following results are obtained:

| Dwell Time | Immediate Tensiles | Cold Tensiles |
|---|---|---|
| 40" | 62 | 318 |
| 50" | 57 | 318 |

EXAMPLE 10

A foundry sand mixture is prepared by admixing sand with the polymeric composition obtained in accordance with Example 2. The amount of binder employed is about one and one-half weight % based upon the amount of sand. Also added to the mixture are silane A-172 in an amount of 3.3% based upon the binder and methyl ethyl ketone peroxide in an amount of 25% by weight based upon the binder. The mix is cured by subjecting it to a flow of $SO_2$ gas for 1 second followed by a 15 second $N_1$ purge.

The results obtained are as follows:

| Tensile Strengths | Psi |
|---|---|
| Immediate | 77 |
| 2 Hours | 172 |
| 3 Hours | 178 |
| 72 Hours | 92 |
| 0 + 72 Hours 100% R.H. | 65 |

EXAMPLE 11

Erosion wedge cores are prepared using the compositions and curing techniques of Examples 4 and 5 hereinabove. The cores are used to have poured therein gray iron at 2700° F. and a 16" height. No erosion is observed.

What is claimed is:

1. Thermosettable polymeric cyclopentadiene derivative having recurring units of the Formula I, or isomers thereof, or mixtures thereof:

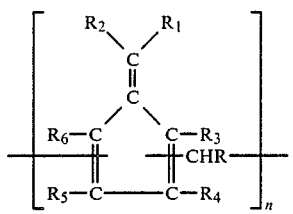

wherein R is hydrogen or an alkyl group having 1–4 carbon atoms; each $R_1$ and $R_2$, individually, is methyl or ethyl, or both $R_1$ and $R_2$ are hydrogen; each $R_3$, $R_4$, $R_5$, and $R_6$, individually, is hydrogen, methyl, —$CH_2$—, or

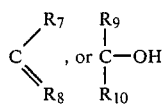

wherein $R_7$ is hydrogen or methyl or ethyl, $R_8$ is methylene or ethylidene; each $R_9$ and $R_{10}$, individually, is hydrogen or methyl or ethyl, provided that 2 of $R_3$, $R_4$, $R_5$, or $R_6$ are —CHR— and that at least 1 of said $R_3$, $R_4$, $R_5$, and $R_6$ is hydrogen and wherein n is at least 2.

2. The derivative of claim 1 wherein at least one of $R_1$ and $R_2$ is methyl.

3. The derivative of claim 1 wherein $R_1$ is methyl and $R_2$ is ethyl.

4. The derivative of claim 1 wherein both $R_1$ and $R_2$ are methyl.

5. The derivative of claim 1 wherein the average n is an integer of about 2 to about 25.

6. The derivative of claim 1 having an average molecular weight of about 200 to about 4000.

7. The derivative of claim 1 wherein R is hydrogen or methyl.

8. The derivative of claim 1 wherein R is hydrogen.

9. A thermosetting composition containing a derivative of claim 1; and a catalytic amount of an acidic catalyst having a pKa of about 4 or less.

10. The composition of claim 9 wherein at least one of $R_1$ and $R_2$ is methyl.

11. The composition of claim 9 wherein $R_1$ is methyl and $R_2$ is ethyl.

12. The composition of claim 9 wherein the average n is an integer of about 2 to about 25.

13. The composition of claim 9 wherein said derivative has an average molecular weight of about 200 to about 4000.

14. The composition of claim 9 wherein the amount of said acidic catalyst is at least about 4% by weight.

15. The composition of claim 9 wherein R is hydrogen or methyl.

16. The composition of claim 9 wherein R is hydrogen.

17. The composition of claim 9 wherein said catalyst is an organic sulfonic acid.

18. A molding composition which comprises a major amount of aggregate and an effective bonding amount up to about 40% by weight of the aggregate of the composition of claim 9.

19. The molding composition of claim 18 which is a foundry composition containing at least about 90% by weight of the aggregate.

20. A process for the fabrication of molded articles which comprises:
    (a) mixing the aggregate with a bonding amount up to about 40% by weight based upon the weight of the aggregate of a composition of claim 9;
    (b) introducing the composition obtained from step (a) into a pattern;
    (c) hardening the composition in the pattern to become self-supporting; and
    (d) thereafter removing the shaped article of step (c) from the pattern and allowing it to further cure, thereby obtaining a hardened, solid, cured, molded article.

21. A process for the fabrication of molded articles which comprises:
    (a) mixing the aggregate with a bonding amount up to about 40% by weight based upon the weight of the aggregate of at least one derivative of claim 1;
    (b) introducing the composition obtained from step (a) into a pattern;
    (c) hardening the composition in the pattern to become self-supporting by passing an acidic gas through the composition; and
    (d) thereafter removing the shaped article of step (c) from the pattern and allowing it to further cure, thereby obtaining a hardened, solid, cured, molded article.

22. A process for preparing thermosettable polymeric cyclopentadiene derivative which comprises reacting at a temperature of about 60° C. or less for up to about 4 hours, a cyclopentadiene derivative having the formula:

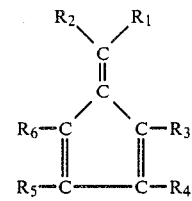

or isomers, or mixtures thereof; wherein each $R_1$ and $R_2$, individually, is methyl or ethyl or both $R_1$ and $R_2$ are hydrogen; each $R_3$, $R_4$, $R_5$, and $R_6$, individually, is hydrogen, methyl,

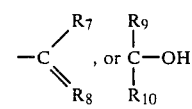

wherein $R_7$ is hydrogen or methyl or ethyl; $R_8$ is methylene or ethylidene; each $R_9$ and $R_{10}$, individually, is hydrogen or methyl or ethyl, and provided that at least three of $R_3$, $R_4$, $R_5$, and $R_6$ are hydrogen; with an aldehyde having 1–5 carbon atoms in the presence of a basic catalyst to provide a thermosettable polymeric cyclopentadiene derivative wherein about 0.1 to about 2 moles of aldehyde per mole of said cyclopentadiene are employed.

23. The process of claim 22 wherein the temperature is about 45°–60° C.

24. The process of claim 22 wherein the time is about one-fourth to about 4 hours.

25. The process of claim 22 wherein the time is about one-half to about 3 hours.

26. The process of claim 22 wherein about 0.5 to about 1.25 moles of aldehyde per mole of said cyclopentadiene derivative are employed.

27. The process of claim 22 wherein said aldehyde is formaldehyde or acetaldehyde.

28. The process of claim 22 wherein said aldehyde is formaldehyde.

29. A polymeric cyclopentadiene derivative obtained by the process of claim 11.

* * * * *